(12) United States Patent
Nycz et al.

(10) Patent No.: US 7,747,306 B2
(45) Date of Patent: Jun. 29, 2010

(54) OSTEOCHONDRAL IMPLANT PROCEDURE

(75) Inventors: Jeffrey H. Nycz, Collierville, TN (US);
Jeetendra Bharadwaj, Memphis, TN (US); Daniel Shimko, Germantown, TN (US)

(73) Assignee: Warsaw Orthopedic, Inc.

( * ) Notice: Subject to any disclaimer, the term of this patent is extended or adjusted under 35 U.S.C. 154(b) by 643 days.

(21) Appl. No.: 11/514,433

(22) Filed: Sep. 1, 2006

(65) Prior Publication Data
US 2008/0097608 A1 Apr. 24, 2008

(51) Int. Cl.
A61B 5/05 (2006.01)
(52) U.S. Cl. .................. 600/407; 600/410; 600/425
(58) Field of Classification Search .............. 600/407, 600/410, 425; 606/102, 281; 623/16.11; 703/11
See application file for complete search history.

(56) References Cited

U.S. PATENT DOCUMENTS

| | | | |
|---|---|---|---|
| 5,383,454 A | 1/1995 | Bucholz |
| 5,851,183 A | 12/1998 | Bucholz |
| 5,871,445 A | 2/1999 | Bucholz |
| 5,891,034 A | 4/1999 | Bucholz |
| 5,919,196 A | 7/1999 | Bobic et al. |
| 5,921,987 A | 7/1999 | Stone |
| 5,964,805 A | 10/1999 | Stone |
| 6,007,496 A | 12/1999 | Brannon |
| D420,132 S | 2/2000 | Bucholz et al. |
| 6,021,343 A | 2/2000 | Foley et al. |
| D422,706 S | 4/2000 | Bucholz |
| 6,110,209 A | 8/2000 | Stone |
| 6,118,845 A | 9/2000 | Simon |
| 6,167,145 A | 12/2000 | Foley et al. |
| 6,190,395 B1 | 2/2001 | Williams |
| 6,226,548 B1 | 5/2001 | Foley et al. |
| 6,235,038 B1 | 5/2001 | Hunter et al. |
| 6,236,875 B1 | 5/2001 | Bucholz et al. |
| 6,253,210 B1 | 6/2001 | Smith et al. |
| 6,306,142 B1 | 10/2001 | Johanson et al. |
| 6,340,363 B1 | 1/2002 | Bolber et al. |
| 6,348,058 B1 | 2/2002 | Melkent et al. |
| 6,375,658 B1 | 4/2002 | Hangody et al. |
| 6,379,302 B1 | 4/2002 | Kessman et al. |
| 6,381,485 B1 | 4/2002 | Hunter et al. |
| 6,395,011 B1 | 5/2002 | Johanson et al. |
| 6,402,762 B2 | 6/2002 | Hunter et al. |
| 6,434,415 B1 | 8/2002 | Foley et al. |
| 6,434,507 B1 | 8/2002 | Clayton et al. |
| 6,440,141 B1 | 8/2002 | Philippon |
| 6,470,207 B1 | 10/2002 | Simon et al. |
| 6,474,341 B1 | 11/2002 | Hunter et al. |
| 6,488,033 B1 | 12/2002 | Cerundolo |
| 6,490,467 B1 | 12/2002 | Bucholz et al. |
| 6,491,699 B1 | 12/2002 | Henderson et al. |
| 6,535,756 B1 | 3/2003 | Simon et al. |

(Continued)

FOREIGN PATENT DOCUMENTS

WO WO9424933 A1 11/1994

(Continued)

*Primary Examiner*—Long V Le
*Assistant Examiner*—Nigel Fontenot

(57) ABSTRACT

A surgical procedure for implanting tissue from a cadaver/autograft bone into a recipient site at an anatomical area of a patient, and a computer-readable medium encoded with a computer program for use in the surgical procedure.

21 Claims, 2 Drawing Sheets

U.S. PATENT DOCUMENTS

| | | |
|---|---|---|
| 6,540,668 B1 | 4/2003 | Schulz et al. |
| 6,553,152 B1 | 4/2003 | Miller et al. |
| 6,592,588 B1 | 7/2003 | Bobic et al. |
| 6,636,757 B1 | 10/2003 | Jascob et al. |
| 6,669,635 B2 | 12/2003 | Kessman et al. |
| 6,708,184 B2 | 3/2004 | Smith et al. |
| 6,725,080 B2 | 4/2004 | Melkent et al. |
| 6,754,374 B1 | 6/2004 | Miller et al. |
| 6,767,354 B2 | 7/2004 | Johanson et al. |
| 6,796,988 B2 | 9/2004 | Melkent et al. |
| 6,801,801 B1 * | 10/2004 | Sati ............................ 600/429 |
| 6,852,114 B2 | 2/2005 | Cerundolo |
| 6,892,090 B2 | 5/2005 | Verard et al. |
| 6,920,347 B2 | 7/2005 | Simon et al. |
| 6,978,166 B2 | 12/2005 | Foley et al. |
| 7,007,699 B2 | 3/2006 | Martinelli et al. |
| RE39,133 E | 6/2006 | Clayton et al. |
| 2004/0034437 A1 | 2/2004 | Schmieding |
| 2004/0039400 A1 | 2/2004 | Schmieding et al. |
| 2004/0059425 A1 | 3/2004 | Schmieding |
| 2004/0176771 A1 | 9/2004 | Schmieding |
| 2004/0193154 A1 | 9/2004 | Leatherbury et al. |
| 2005/0101962 A1 | 5/2005 | Schwenke et al. |
| 2005/0222687 A1 | 10/2005 | Vunjak-Novakovic et al. |
| 2006/0060209 A1 | 3/2006 | Shepard |
| 2007/0276224 A1 * | 11/2007 | Lang et al. .................. 600/410 |

FOREIGN PATENT DOCUMENTS

| | | | |
|---|---|---|---|
| WO | WO9611624 | A2 | 4/1996 |

* cited by examiner

OSTEOCHONDRAL IMPLANT PROCEDURE

BACKGROUND

This invention relates to an improved surgical procedure for implanting tissue from a cadaver/autograft bone into a recipient site at an anatomical area of a patient.

There are several surgical procedures in place in which host tissue is replaced with cadaver/autograft tissue. For example, in osteochondral replacement, hip and shoulder arthroscopies, ankle and TMJ procedures, a cadaver/autograft tissue is harvested for implanting in the host bone. In these procedures it is essential that the cadaver/autograft tissue match the anatomic surface of the host bone. More specifically, the tissues must be properly mapped to ensure congruent anatomic surfaces between the host and the cadaver/autograft tissues.

According to an embodiment of the invention, a process to map anatomic structures is provided to facilitate accurate harvesting of cadaver/autograft tissue using various imaging modalities, computer modeling and automated database selection of tissue.

DETAILED DESCRIPTION

The present invention will be described, for the purpose of example, in connection with an osteochondral replacement, it being understood that it is equally applicable to procedures involving other areas of the anatomy such as hip and shoulder arthroscopies, as well as ankle and TMJ procedures.

Figure 1:
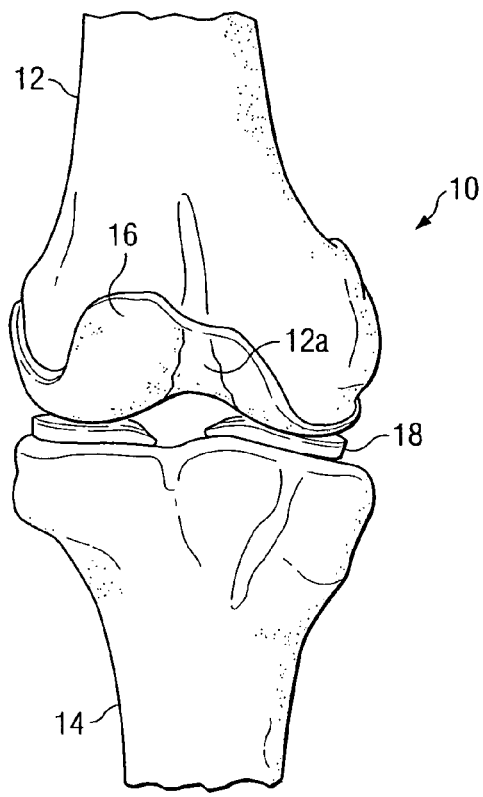
FIG. 1 is an elevational view of a knee with certain parts removed in the interest of clarity.

Referring to FIG. 1 of the drawing, the reference numeral 10 refers, in general, to a knee of a human including a femur 12 and a tibia 14 whose respective chondral areas are in close proximity. A cartilage 16 extends over a portion of the chondral area of the femur 12, and a meniscus 18 extends between the cartilage and the tibia 14. The patella, as well as the tendons, ligaments, and quadriceps that also form part of the knee 10, are not shown in the interest of clarity.

It will be assumed that a portion of the cartilage 16 extending over a chondral area of the femur 12, has been damaged and removed by the surgeon, or has worn away, leaving a defect, or recipient site, 12a. Thus, the procedure according to an embodiment of the invention will be described in connection with implanting a tissue from another area of the patient, from a donor, or from a cadaver in the recipient site.

To this end, one or more openings (not shown) are formed at the recipient site 12a and extend from the condyle of the recipient site 12a into the corresponding chondral area of the femur 12. Each opening is adapted to receive a tissue in a manner to be described. The tissue(s) is harvested from another area of the patient/recipient, such as an undamaged non-load bearing area of the femur or tibia, or from a corresponding area of a donor or cadaver in accordance with known techniques. The tissue(s) is sized so as to be implantable in the opening(s) at the recipient site in accordance with known techniques, and an embodiment of the invention involves mapping of the cadaver/autograft tissues and the recipient site to ensure congruent anatomic surfaces.

Figure 2:
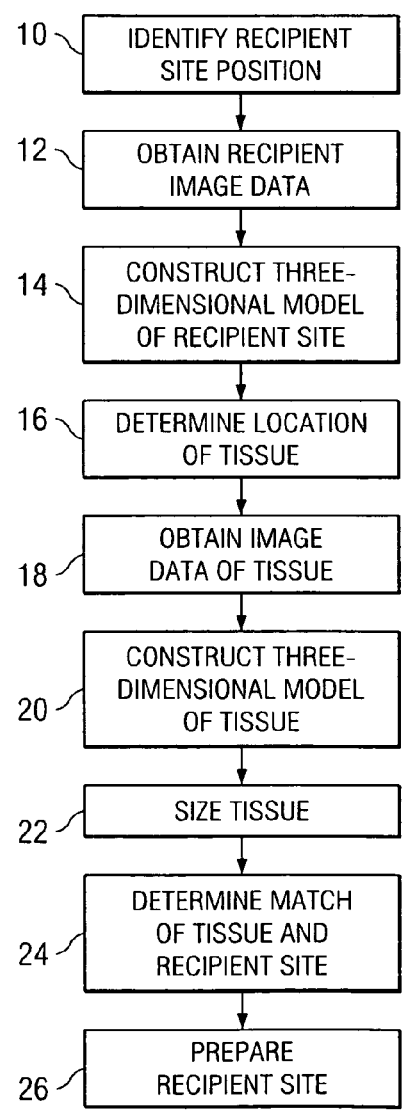
FIG. 2 is a flow diagram depicting steps of a surgical procedure on the knee according to an embodiment of the invention.

To this end, and referring to FIG. 2, a computer readable medium is provided that is encoded with a computer program including instructions for performing several steps that are described below.

According to step 10, the position of the recipient site is initially identified based on anatomical structures and the site is oriented to a common datum.

According to step 12, image data of the recipient site is obtained using magnetic resonance imaging and/or computed tomography (CT scan and CAT scan).

According to step 14, a three-dimensional model of the recipient site is constructed based on the image data.

According to step 16, the location and geometric boundaries of the cadaver/autograft tissue is determined.

According to step 18, image data of the tissue is obtained using magnetic resonance imaging and/or computed tomography (CT scan and CAT scan).

According to step 20, a three-dimensional model of the tissue is constructed based on the image data obtained in step 18.

According to step 22, the tissue is properly sized by driving computerized, numerically-controlled machine tools or robotics based on the image data obtained in step 18 and the model of step 20. According to step 24, a geometric analysis is made to determining an appropriate geometric match of the tissue with the recipient site based on the above models as well as data stored in a database.

According to step 26, the recipient site is prepared by image guidance based on the model of the site obtained in step 14 so that the site will accept the tissue.

After the above has been completed, the tissue is harvested based on the geometric match of step 24, above, and the harvested tissue is implanted in the recipient site.

As stated above, the replacement of tissue in the knee has been described above for the purposes of example only, it being understood that it is equally applicable to procedures involving other areas of the anatomy such as hip and shoulder arthroscopies, as well as ankle and TMJ procedures.

Figure 3:
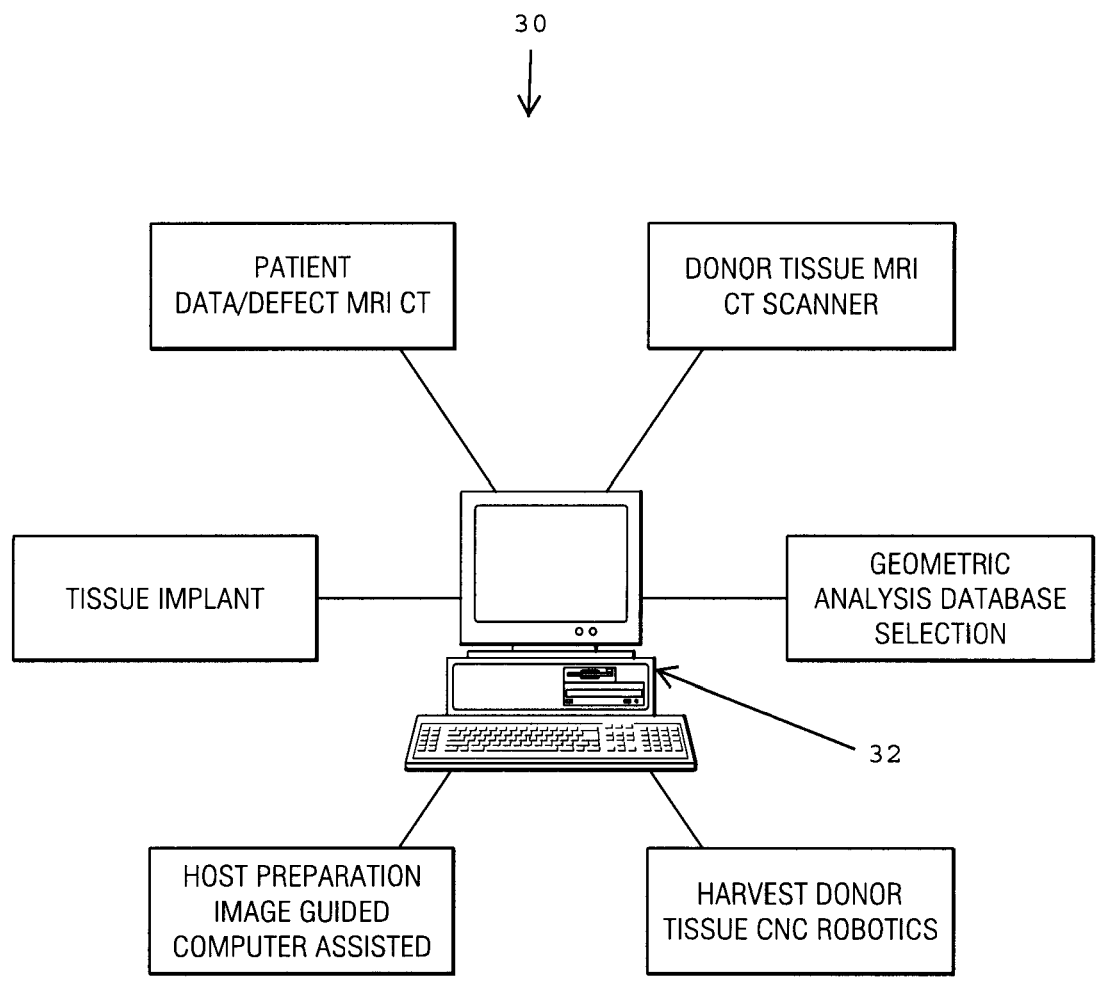

It is understood that a computer network can serve as the computer-readable medium described above. Such a network is shown, in general by the reference numeral 30 in FIG. 3, and includes a computer 32 associated with the computer readable medium identified in the drawing so as to implement the steps listed above. It is understood that the computer readable medium can be distributed across many different mechanisms, e.g., a first part stored in a first memory unit of a first computer, a second part stored in a second memory unit of a second computer, and so on.

Those skilled in the art will readily appreciate that many variations and modifications of the embodiment described above can be made without materially departing from the novel teachings and advantages of this invention. Accordingly, all such variations and modifications are intended to be included within the scope of this invention as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A surgical procedure for implanting autograft bone tissue from a site different from a recipient site into the recipient site at an anatomical area of a patient, the procedure comprising:
   obtaining image data of the recipient site;
   constructing a three-dimensional model of the recipient site based on the image data;
   obtaining image data of the autograft bone tissue from the site different from the recipient site;
   constructing a three-dimensional model of the autograft bone tissue from the site different from the recipient site based on the latter image data;
   determining an appropriate geometric match of the autograft bone tissue with the recipient site based on the above models;
   harvesting the autograft bone tissue from the site different from the recipient site based on the geometric match; and
   implanting the harvested autograft bone tissue from a site different from the recipient site into the recipient site.

2. The procedure of claim 1 further comprising identifying the position of the recipient she based on anatomical structures and orienting the site to a common datum.

3. The procedure of claim 1 obtaining the image data of the recipient site using magnetic resonance imaging, computed tomography or combination of both.

4. The procedure of claim 1 further comprising determining the location and geometric boundaries of said autograft bone tissue before the second step of obtaining.

5. The procedure of claim 1 further comprising obtaining the image data of said autograft bone tissue using magnetic resonance imaging, computed tomography or a combination of both.

6. The procedure of claim 1 further comprising properly sizing said autograft bone tissue by driving computerized, numerically-controlled machine tools or robotics based on the image data of the tissue and the model of said autograft bone tissue.

7. The procedure of claim 1 further comprising determining the appropriate geometric match of said autograft bone tissue with the recipient site based on data stored in a database.

8. The procedure of claim 1 further comprising preparing the recipient site by image guidance based on the model of the site.

9. A non-transitory computer-readable medium encoded with a computer program for use in a surgical procedure for implanting autograft bone tissue from a site different from the recipient site into the recipient she at an anatomical area of a patient, the computer program comprising instructions for:
   obtaining image data of the recipient site;
   constructing a three-dimensional model of the recipient site based on the image data;
   obtaining image data of the autograft bone tissue from the site different from the recipient site;
   constructing a three-dimensional model of the autograft bone tissue from the site different from the recipient site based on the latter image data; and
   determining an appropriate geometric match of the autograft bone tissue from the site different from the recipient site with the recipient she based on the above models.

10. The medium of claim 9 further comprising instructions for identifying the position of the recipient she based on anatomical structures and orienting the site to a common datum.

11. The medium of claim 9 further comprising instructions for obtaining the image data of the recipient site using magnetic resonance imaging, computed tomography or a combination thereof.

12. The medium of claim 9 further comprising instructions for determining the location and geometric boundaries of said autograft bone tissue before the second step of obtaining.

13. The medium of claim 9 further comprising instructions for obtaining the image data of said autograft bone tissue using magnetic resonance imaging, computed tomography or a combination thereof.

14. The medium of claim 9 further comprising instructions for properly sizing said autograft bone tissue by driving computerized, numerically-controlled machine tools or robotics based on the image data of the tissue and the model of said autograft bone tissue.

15. The medium of claim 9 further comprising determining the appropriate geometric match of said autograft bone tissue with the recipient site based on data stored in a database.

16. The medium of claim 9 further comprising instructions for preparing the recipient site by image guidance based on the model of the site.

17. The medium of claim 9 wherein the tissue is harvested based on the geometric match, and the harvested said autograft bone tissue is implanted in the recipient site.

18. A surgical procedure for implanting cadaver tissue from into the recipient site at an anatomical area of a patient, the procedure comprising:
   obtaining image data of the recipient site;
   constructing a three-dimensional model of the recipient site based on the image data;
   obtaining image data of the cadaver tissue;
   constructing a three-dimensional model of the cadaver tissue based on the latter image data;
   determining an appropriate geometric match of the cadaver tissue based on the above models;
   harvesting the cadaver tissue based on the geometric match; and implanting the harvested cadaver tissue into the recipient site.

19. The procedure of claim 18 further comprising obtaining the image data of the cadaver tissue using magnetic resonance imaging, computed tomography or a combination of both.

20. A non-transitory computer-readable medium encoded with a computer program for use in a surgical procedure for implanting cadaver tissue into the recipient site at an anatomical area of a patient, the computer program comprising instructions for:
   obtaining image data of the recipient site;
   constructing a three-dimensional model of the recipient site based on the image data;
   obtaining image data of the cadaver tissue;
   constructing a three-dimensional model of the cadaver tissue based on the latter image data; and
   determining an appropriate geometric match of the cadaver tissue with the recipient site based on the above models.

21. The medium of claim 20 further comprising instructions for obtaining the image data of the recipient site using magnetic resonance imaging, computed tomography or a combination thereof.

* * * * *